United States Patent
Lin

(10) Patent No.: US 8,506,938 B2
(45) Date of Patent: Aug. 13, 2013

(54) COMPOUND APPLYING TO SKIN AND A METHOD MAKING THE SAME

(76) Inventor: Hsien-wen Lin, Chiayi (TW)

( * ) Notice: Subject to any disclaimer, the term of this patent is extended or adjusted under 35 U.S.C. 154(b) by 151 days.

(21) Appl. No.: 13/218,878

(22) Filed: Aug. 26, 2011

(65) Prior Publication Data

US 2013/0052147 A1  Feb. 28, 2013

(51) Int. Cl.
- *A61K 8/00* (2006.01)
- *A61K 8/49* (2006.01)
- *A61K 33/12* (2006.01)
- *A61Q 5/12* (2006.01)
- *A61L 9/04* (2006.01)

(52) U.S. Cl.
USPC ........ 424/59; 424/70.9; 424/70.12; 424/76.4; 424/683

(58) Field of Classification Search
None
See application file for complete search history.

(56) References Cited

FOREIGN PATENT DOCUMENTS

| | | |
|---|---|---|
| TW | 345496 | 11/1998 |
| TW | 482683 | 4/2002 |
| TW | 201002358 | 1/2010 |
| TW | 201100124 | 1/2011 |
| WO | WO 9641614 A1 * | 12/1996 |

* cited by examiner

*Primary Examiner* — Michael G Hartley
*Assistant Examiner* — Nabila Ebrahim
(74) *Attorney, Agent, or Firm* — Muncy, Geissler, Olds & Lowe, PLLC

(57) ABSTRACT

A compound applying to skin and a method making the same comprises certain proportions for following first components: Dimethicone Crosspolymer, Dimethicone/Vinyl Dimethicone Crosspolymer, Cyclotetrasiloxane, Dimethicone, Cetyl PEG/PPG-15/15 Butyl Ether Dimethicone, Squalane, and Titanium Dioxide. Second components, third components, and fourth components with specific proportions as claimed are timely added in the first components. Sequentially mixing, heating, and dissolving the afore components would bring about the compound that keeps skin from sun exposure and provides functions of moisturizing, anti-wrinkle, spots clearing, blushers, anti-acnes, and whitening.

1 Claim, No Drawings

COMPOUND APPLYING TO SKIN AND A METHOD MAKING THE SAME

BACKGROUND OF THE INVENTION

1. Field of the Invention

The present invention relates to a compound applying to skin and a method making the same, which is especially anti-irritation, avoids blocking pores, prevents oily skin, and benefits the skin care.

2. Description of the Related Art

Proper daily skin care is good to lighten users' appearances, and they can look healthier, younger and more confident. In the general beauty care, products of sun-screening, moisturizing, anti-wrinkle are most popular ones. Another products like the spots clear, blusher, anti-acnes product, whitening product, and others that improve users' skin are also welcome in the market.

Wherein, the object for applying the sun-screening product is to avoid the ultraviolet rays in the sun ruining the skin, since exposing the skin to the sun may result in the dry skin, ageing cells, and even pathological cells. The object for applying the moisturizing and anti-wrinkle products is to firm the skin, so that users may look healthier and younger. Appropriately applying spots clearing products and blushers may especially enhance women's attraction.

A disclosed patent No. TW482683 "SUNSCREEN COMPOSITION" and a disclosed publication No. TW201002358 "SUN PROTECTION COMPOSITIONS" are both related to sun-screening products. Other disclosed patent No. TW201100124 "SKIN CARE COMPOSITION" and publication No. TW345496 "SKIN CARE COMPOSITION CONTAINING RETINOL" are both related to skin care products.

In fact, components in the sun-screening products and other like skin care products commonly incur irritation on the skin. Accordingly, users allergic to the irritating products may easily ruin their skin. Therefore, many producers of the skin care products endeavor to develop new skin care composition that contains low irritating factors to the skin so as to prevent hypersensitivity.

SUMMARY OF THE INVENTION

The present invention is to provide a novel compound applying to skin and a novel method making the same. Applying afore compound to the skin decreases the chance of damaging the skin from the ultraviolet. Thereby, the skin is protected, and concurrently, the allergic reaction could be reduced. While essences of various plants and humectant as well as moisturizing components are properly added, the compound is especially beneficial to ameliorate users' skin.

The compound in accordance with the present invention mainly comprises first components by different weight percentages as follows: 10% to 70% of Dimethicone Crosspolymer, 5% to 20% of Dimethicone/Vinyl Dimethicone Crosspolymer, 7% to 60% of Cyclotetrasiloxane, 4.2% to 60% of Dimethicone, 0.1% to 5% of Cetyl PEG/PPG-15/15 Butyl Ether Dimethicone, 1% to 10% of Squalane, and 1% to 15% of Titanium Dioxide.

Preferably, the compound further comprises second components by different weight percentages as follows: 0.01% to 2% of Silica, 0.01% to 2% of Silica Dimethyl Silylate, and 5% to 60% of Isododecane.

Preferably, the compound further comprises third components by different weight percentages as follows: 0.5% to 10% of Trimethylsiloxysilicate, 1% to 10% of C12-15 Alkyl benzoate, and 1% to 10% of 2-Ethylhexy Palmitate.

Preferably, the compound further comprises fourth components by different weight percentages as follows: 1% to 15% of 1, 3 Propylene glycol, 1% to 20% of magnesium silicate, and 1% to 20% of Mica.

Preferably, an additive is properly added. The additive includes components by different weight percentages as follows: 0.01% to 5% of Iron Oxide black, 0.01% to 5% of Iron Oxide yellow, 0.01% to 5% of Iron Oxide red, 0.005% to 1% of Tartrazine Aluminum Lake, 0.005% to 1% of Erythrosine Aluminum Lake, 1% to 20% of Magnesium stearate, 0.05% to 0.5% of Chlorhexidine Gluconate, 0.01% to 3% of Ginseng Fragrant Oil, 0.01% to 3% of Angelica Fragrant Oil, 0.01% to 3% of Chuanxiong Fragrant Oil, 0.01% to 3% of Wolfberry Fragrant Oil, 0.01% to 5% of Duhuo Fragrant Oil, 0.01% to 5% of Sandalwood Fragrant Oil, 0.01% to 5% of Cinnamon Fragrant Oil, 0.01% to 3% of Ginger Fragrant Oil, and 0.01% to 0.05% of Butylated hydroxytoluene.

A method making afore compound applying to skin comprises steps of:

A. Combining afore magnesium silicate, Iron Oxide black, Iron Oxide yellow, Iron Oxide red, Titanium Dioxide, Mica, Tartrazine Aluminum Lake, Erythrosine Aluminum Lake, and Magnesium stearate to form a compound; B. Combining and heating afore Silica Dimethyl Silylate, Trimethylsiloxysilicate, Isododecane, Cyclotetrasiloxane, C12-15 Alkyl benzoate, Dimethicone, 2-Ethylhexyl Palmitate, Squalane, and Butylated hydroxytoluene until a temperature reaches 40 to 50 Celsius degrees; after the Trimethylsiloxysilicate and the Butylated hydroxytoluene are dissolved, the compound in step A is poured therein and evenly mixed therewith to form into a first mixed solution; C. Adding afore Dimethicone Crosspolymer, Dimethicone/Vinyl Dimethicone Crosspolymer, and Silica into mixed solution as described in Step B to form into a second mixed solution; D. Combining afore 1,3-Propylene glycol and Chlorhexidine Gluconate to form into a combined solution and dissolving the combined solution below 40 to 50 Celsius degrees, thereby adding the combined solution that is dissolved into the second mixed solution as described in Step C to form into a third mixed solution; E. Adding and evenly mixing afore Cetyl PEG/PPG-15/15 Butyl Ether Dimethicone into the third mixed solution as described in step D to form into a fourth mixed solution; and F. Adding and evenly mixing afore Ginseng Fragrant Oil, Angelica Fragrant Oil, Chuanxiong Fragrant Oil, Wolfberry Fragrant Oil, Duhuo Fragrant Oil, Sandalwood Fragrant Oil, Cinnamon Fragrant Oil, and Ginger Fragrant Oil into the fourth mixed solution as described in step E.

Preferably, a sieve with 150 to 1000 meshes is utilized to sieve the compound.

The present invention has the following advantages:

1. The skin is limited from sun exposure, so the skin would not be irritated, which preferably reduces the allergic reaction.

2. The essences of various plants and the components that moisturize skin are beneficial for skin care.

3. Functions like protecting skin from sun exposure, moisturizing, anti-wrinkle, covering spots and applying blusher, anti-acnes, and whitening are achievable.

BRIEF DESCRIPTION OF THE DRAWINGS

None

DETAILED DESCRIPTION OF THE PREFERRED EMBODIMENTS

Following embodiments are depicted details of the present invention.

A compound applying to skin mainly comprises first components by different weight percentages as follows: 10% to 70% of Dimethicone Crosspolymer, 5% to 20% of Dimethicone/Vinyl Dimethicone Crosspolymer, 7% to 60% of Cyclotetrasiloxane, 4.2% to 60% of Dimethicone, 0.1% to 5% of Cetyl PEG/PPG-15/15 Butyl Ether Dimethicone, 1% to 10% of Squalane, and 1% to 15% of Titanium Dioxide.

Besides afore first components, second components, third components, and fourth components are also added as follows:

The compound further comprises second components by different weight percentages as follows: 0.01% to 2% of Silica, 0.01% to 2% of Silica Dimethyl Silylate, and 5% to 60% of Isododecane. The compound further comprises third components by different weight percentages as follows: 0.5% to 10% of Trimethylsiloxysilicate, 1% to 10% of C12-15 Alkyl benzoate, and 1% to 10% of 2-Ethylhexy Palmitate. The compound further comprises fourth components by different weight percentages as follows: 1% to 15% of 1, 3 Propylene glycol, 1% to 20% of magnesium silicate, and 1% to 20% of Mica.

An additive is properly added. The additive includes components by different weight percentages as follows: 0.01% to 5% of Iron Oxide black, 0.01% to 5% of Iron Oxide yellow, 0.01% to 5% of Iron Oxide red, 0.005% to 1% of Tartrazine Aluminum Lake, 0.005% to 1% of Erythrosine Aluminum Lake, 1% to 20% of Magnesium stearate, 0.05% to 0.5% of Chlorhexidine Gluconate, 0.01% to 3% of Ginseng Fragrant Oil, 0.01% to 3% of Angelica Fragrant Oil, 0.01% to 3% of Chuanxiong Fragrant Oil, 0.01% to 3% of Wolfberry Fragrant Oil, 0.01% to 5% of Duhuo Fragrant Oil, 0.01% to 5% of Sandalwood Fragrant Oil, 0.01% to 5% of Cinnamon Fragrant Oil, 0.01% to 3% of Ginger Fragrant Oil, and 0.01% to 0.05% of Butylated hydroxytoluene.

Please be noted:

In the first components, the Dimethicone Crosspolymer is served as an emulsion stabilizer, the Dimethicone/Vinyl Dimethicone Crosspolymer is served as a lipophilic thickening agent, the Cyclotetrasiloxane is served as a solvent of afore components, the Dimethicone is served as a waterproof film, the Cetyl PEG/PPG-15/15 Butyl Ether Dimethicone is served as an emulsifier, the Squalane is served as a skin softener and wetter, and the Titanium Dioxide is served as a sun-screening agent.

In the second components, the Silica is served as a polishing agent, the Silica Dimethyl Silylate is served for oil control, and the Isododecane is served as a solvent.

In the third components, the Trimethylsiloxysilicate is served as a waterproof film and waterproofing, the C12-15 Alkyl benzoate is served as a skin softener, and the 2-Ethylhexyl Palmitate is served as a keratolytics agent.

In the fourth components, the 1,3-Propylene glycol is served as a humectant, the magnesium silicate is served as an emulsifier, and the Mica 19 is served for moisturizing and a colorant.

Additionally, in the additive, the Iron Oxide black, the Iron Oxide yellow, the Iron Oxide red, the Tartrazine Aluminum Lake, and the Erythrosine Aluminum Lake are served as a pigment. The Magnesium stearate is served as a colorant, the Chlorhexidine Gluconate is served as a bacteriostat, the Ginseng Fragrant Oil is served as an antioxidant and for firming skin, the Angelica Fragrant Oil is served for whitening and as an antioxidant, the Chuanxiong Fragrant Oil is served for moisturizing and whitening, the Wolfberry Fragrant Oil is served as an antioxidant and for anti-wrinkle, the Duhuo Fragrant Oil is served for anti-inflammation and moisturizing, the sandalwood Fragrant Oil is served for anti-inflammation, the Cinnamon Fragrant Oil is served for whitening and as an antioxidant, the Ginger Fragrant Oil is served as an antioxidant, and the Butylated hydroxytoluene is served as an antioxidant.

Thereby, the compound of the present invention favorably protects skin from sun exposure, which decreases the chance of irritation and allergic reaction, so this product is especially suitable for users who stay outdoors for a long time. Adding the essences of various plants and other moisturizers in the product especially leaves the skin delicate and elastic. As a result, the skin maintains healthy and ruddy. Accordingly the compound of the present invention is beneficial for daily skin care. While afore pigments are properly added in the compound with suitable proportions, the compound is further served as the spots clearer and the blusher.

A method making afore compound comprises steps of:

A. Combining afore magnesium silicate, Iron Oxide black, Iron Oxide yellow, Iron Oxide red, Titanium Dioxide, Mica, Tartrazine Aluminum Lake, Erythrosine Aluminum Lake, and Magnesium stearate to form a compound, thereby utilizing a sieve with 150 to 1000 meshes to sieve the compound;

B. Combining and heating afore Silica Dimethyl Silylate, Trimethylsiloxysilicate, Isododecane, Cyclotetrasiloxane, C12-15 Alkyl benzoate, Dimethicone, 2-Ethylhexyl Palmitate, Squalane, and Butylated hydroxytoluene until a temperature reaches 40 to 50 Celsius degrees; after the Trimethylsiloxysilicate and the Butylated hydroxytoluene are dissolved, the compound in step A is poured therein and evenly mixed therewith to form into a first mixed solution;

C. Adding afore Dimethicone Crosspolymer, Dimethicone/Vinyl Dimethicone Crosspolymer, and Silica into mixed solution as described in Step B to form into a second mixed solution;

D. Combining afore 1,3-Propylene glycol and Chlorhexidine Gluconate to form into a combined solution and dissolving the combined solution below 40 to 50 Celsius degrees, thereby adding the combined solution that is dissolved into the second mixed solution as described in Step C to form into a third mixed solution;

E. Adding and evenly mixing afore Cetyl PEG/PPG-15/15 Butyl Ether Dimethicone into the third mixed solution as described in step D to form into a fourth mixed solution; and F. Adding and evenly mixing afore Ginseng Fragrant Oil, Angelica Fragrant Oil, Chuanxiong Fragrant Oil, Wolfberry Fragrant Oil, Duhuo Fragrant Oil, Sandalwood Fragrant Oil, Cinnamon Fragrant Oil, and Ginger Fragrant Oil into the fourth mixed solution as described in step E.

Above embodiments demonstrate the inventive steps of the present invention for the patentability. Embodiments presented in the present invention do not limit the creative, novel, and non-obvious spirits involved in the techniques and functions of the same.

I claim:

1. A method for making a composition for applying to skin comprising first components by weight percentages as follows: 10% to 70% of dimethicone crosspolymer, 5% to 20% of dimethicone/vinyl dimethicone crosspolymer, 7% to 60% of cyclotetrasiloxane, 4.2% to 60% of dimethicone, 0.1% to 5% of cetyl PEG/PPG-15/15 butyl ether dimethicone, 1% to 10% of squalane, and 1% to 15% of titanium dioxide, said composition further comprising second components by weight percentages as follows: 0.01% to 2% of silica, 0.01% to 2% of silica dimethyl silylate, and 5% to 60% of isododecane, said composition further comprising third components by weight percentages as follows: 0.5% to 10% of trimethylsiloxysilicate, 1% to 10% of C12-15 alkyl benzoate, and 1% to 10% of 2-ethylhexy palmitate, said composition further comprising fourth components by weight percentages as follows: 1% to 15% of 1, 3 propylene glycol, 1% to 20% of magnesium silicate, and 1% to 20% of mica, wherein an additive is added, said additive including components by weight percentages as follows: 0.01% to 5% of iron oxide black, 0.01% to 5% of iron oxide yellow, 0.01% to 5% of iron oxide red, 0.005% to 1% of tartrazine aluminum Lake, 0.005% to 1% of erythrosine aluminum lake, 1% to 20% of magnesium stearate, 0.05% to 0.5% of chlorhexidine gluconate, 0.01% to 3% of ginseng fragrant oil, 0.01% to 3% of angelica fragrant oil, 0.01% to 3% of chuanxiong fragrant oil, 0.01% to 3% of wolfberry fragrant oil, 0.01% to 5% of duhuo fragrant oil, 0.01% to 5% of sandalwood fragrant oil, 0.01% to 5% of cinnamon fragrant oil, 0.01% to 3% of ginger fragrant oil, and 0.01% to 0.05% of butylated hydroxytoluene;

the method comprising the steps of:

A. combining the magnesium silicate, iron oxide black, iron oxide yellow, iron oxide red, titanium dioxide, mica, tartrazine aluminum lake, erythrosine aluminum lake, and magnesium stearate to form composition, and utilizing a sieve with 150 to 1000 meshes to sieve said composition;

B. combining and heating the silica dimethyl silylate, trimethylsiloxysilicate, isododecane, cyclotetrasiloxane, C12-15 alkyl benzoate, dimethicone, 2-ethylhexyl palmitate, squalane, and butylated hydroxytoluene until a temperature reaches 40 to 50 Celsius degrees; after said trimethylsiloxysilicate and said butylated hydroxytoluene are dissolved, said composition as described in step A is poured therein and evenly mixed therewith to form into a first mixed solution;

C. adding dimethicone crosspolymer, dimethicone/vinyl dimethicone crosspolymer, and silica into mixed solution as described in step B to form into a second mixed solution;

D. combining 1,3-propylene glycol and chlorhexidine gluconate to form into a combined solution and dissolving said combined solution below 40 to 50 Celsius degrees, thereby adding said combined solution that is dissolved into said second mixed solution as described in step C to form into a third mixed solution;

E. adding and evenly mixing cetyl PEG/PPG-15/15 butyl ether dimethicone into said third mixed solution as described in step D to form into a fourth mixed solution; and F. adding and evenly mixing ginseng fragrant oil, angelica fragrant oil, chuanxiong fragrant oil, wolfberry fragrant oil, duhuo fragrant oil, sandalwood fragrant oil, cinnamon fragrant oil, and ginger fragrant oil into said fourth mixed solution as described in step E.

* * * * *